US010905292B2

(12) United States Patent
DeBlasi (10) Patent No.: US 10,905,292 B2
(45) Date of Patent: Feb. 2, 2021

(54) PORTABLE HYGIENE DEVICE (71) Applicant: Richard DeBlasi, Little Silver, NJ (US)

(72) Inventor: Richard DeBlasi, Little Silver, NJ (US)

(*) Notice: Subject to any disclaimer, the term of this patent is extended or adjusted under 35 U.S.C. 154(b) by 0 days.

(21) Appl. No.: 16/718,583

(22) Filed: Dec. 18, 2019

(65) Prior Publication Data
US 2020/0121136 A1 Apr. 23, 2020

Related U.S. Application Data (63) Continuation-in-part of application No. 16/154,271, filed on Oct. 8, 2018.

(60) Provisional application No. 62/570,021, filed on Oct. 9, 2017.

(51) Int. Cl.
A61M 3/02 (2006.01)
A47K 7/08 (2006.01)
A46B 5/02 (2006.01)
A46B 9/02 (2006.01)
A46B 1/00 (2006.01)
A46B 11/00 (2006.01)

(52) U.S. Cl.
CPC ............... A47K 7/08 (2013.01); A46B 1/00 (2013.01); A46B 5/02 (2013.01); A46B 9/025 (2013.01); A46B 9/026 (2013.01); A46B 9/028 (2013.01); A46B 11/0041 (2013.01); A61M 3/0262 (2013.01); A46B 2200/10 (2013.01)

(58) Field of Classification Search
CPC ......... A61M 3/0262; A47K 7/08; A47K 7/00; A47K 7/02; A47K 7/04; A47K 7/043; A46B 5/02; A46B 9/025; A46B 9/026; A46B 9/028; A46B 1/00; A46B 11/0041; A46B 2200/10; A46B 11/002; A46B 2200/1006
USPC .......................... 401/183, 184, 185, 278, 282
See application file for complete search history.

(56) References Cited

U.S. PATENT DOCUMENTS

| 1,113,843 | A | | 10/1914 | Smith | |
|---|---|---|---|---|---|
| 3,734,106 | A | | 5/1973 | Zimmerman | |
| 3,763,850 | A | | 10/1973 | Gaudebout et al. | |
| 4,620,528 | A | | 11/1986 | Arraval | |
| 5,186,563 | A | * | 2/1993 | Gebhard | A46B 11/0027 222/214 |
| 5,310,068 | A | * | 5/1994 | Saghri | B65D 1/0292 215/12.1 |
| 6,039,491 | A | | 3/2000 | Badillo | |
| 6,058,524 | A | | 5/2000 | Deveer | |
| 6,905,274 | B2 | * | 6/2005 | Zwaert | B05C 17/002 401/185 |
| 7,093,993 | B2 | | 8/2006 | Skoog | |
| 7,594,775 | B1 | | 9/2009 | Yoo | |
| 8,979,410 | B2 | | 3/2015 | Massimi | |
| 2004/0037613 | A1 | * | 2/2004 | King | B43L 25/04 401/290 |

* cited by examiner

Primary Examiner — David J Walczak
(74) Attorney, Agent, or Firm — John Maldjian; Maldjian Law Group LLC (57) ABSTRACT A personal hygiene device includes a bottle body configured to hold a fluid, and an extension tube, connected to the bottle body through a connector. In some embodiments, the extension tube includes a brush and an orifice configured to release the fluid. In other embodiments, the extension tube is designed to be inserted into a body cavity and does not include a brush.

19 Claims, 10 Drawing Sheets

PORTABLE HYGIENE DEVICE

CROSS-REFERENCE TO RELATED APPLICATION

This application is a Continuation-in-Part of application Ser. No. 16/154,271, filed Oct. 8, 2018, which claims the benefit of U.S. Provisional Patent Application Ser. No. 62/570,021, filed on Oct. 9, 2017, the entire content of each of the application is hereby incorporated by reference in its entirety.

BACKGROUND

Field of Invention

The following description relates to a portable hygiene device, and to a structural innovation that allows the convenience of cleansing without toilet paper after toilet use.

Description of Related Art

Constipation is a common problem faced by patients with spinal injury, fractured discs, muscle injuries or other disabilities, and by many residents in inpatient hospitals and nursing homes. Reduction in mobility throughout the life span of a person and the increased incidence of obesity are contributing to an increasing number of people who find the use of toilet an unpleasant experience. Further, the stress of society is causing irritable bowel syndrome in millions of people worldwide. With advancements in medicine, the diagnoses of inflammatory bowel diseases such as Crohn's disease and ulcerative colitis, and irritable bowel syndromes result in many people who are faced with managing their gastrointestinal symptoms throughout their lifetime. In addition, diseases such as vaginismus and varices require proper cleanliness and hygiene for men and women in a genital, a urinary, and an anal area, which may otherwise contribute to additional health problems.

Figure 1:
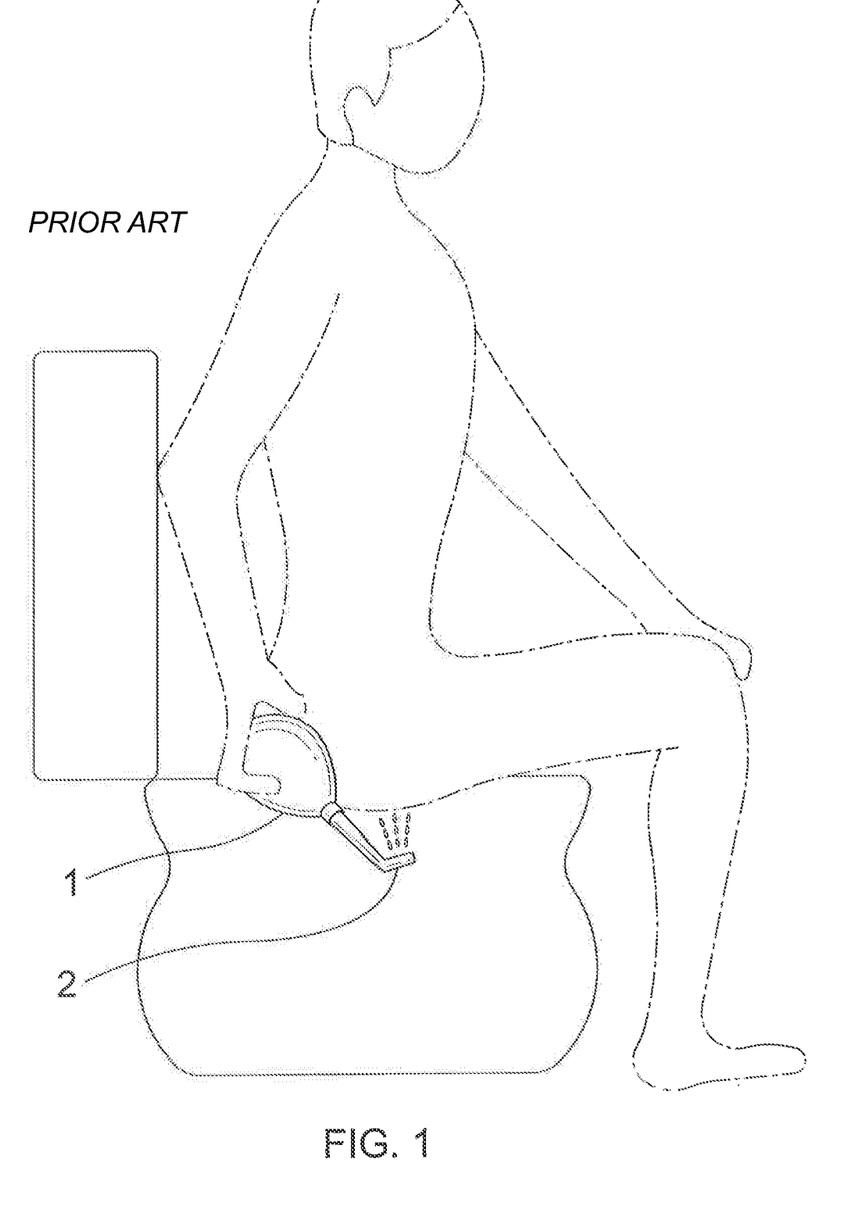
FIG. 1 is a diagram illustrating a conventional personal hygiene device.

As shown in FIG. 1, the portable hygiene device currently known includes a bottle body 1 and a spray head 2, wherein the bottle body 1 is internally hollow and has an opening that connects to the spray head 2 such that water in the bottle body 1 flows through the spray head 2, and into the rectal area.

Through above said structure, a person may spray water through the spray head 2 on the rectal area by squeezing the bottle body with one or both hands after using the toilet. In the event that the rectal area is not sufficiently cleansed by the spraying of water, the remaining soil must be cleaned with a toilet paper or by hand. Further, the conventional portable hygiene devices do not have any mechanism to eliminate refractory period to eject more water. Furthermore, the conventional portable hygiene devices do not have a brush feature for cleaning a genital, a urinary, or an anal area. Moreover, such conventional portable hygiene devices cannot be used for other dysfunctions of constipation and vaginismus.

However, many patients with spinal injury, back issues or other disabilities find it difficult to reach the rectal area with the remaining hand while spraying the water. Furthermore, applying toilet paper may cause irritation in the rectal area, and wiping with hands instead of toilet paper can be unpleasant for the user. Given the frequency with which patients must undergo these ordeals throughout the day, a better way to cleanse oneself is increasingly desired by many people.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a personal hygiene device includes a bottle body configured to hold fluid, an extension tube that forms an elongated portion connected to the bottle body and having one or more orifice configured to release the fluid, and a brush disposed on an outer surface of the extension tube.

The brush may be configured to cleanse a rectal area of a user after a toilet use.

Strands of the brush may have a thickness of 3 mm or greater, and the strands may comprise silicon, rubber, or soft plastic.

The one or more orifice may be disposed at a tip of the extension tube.

The brush may be distanced from a tip of the extension tube by 5 mm or greater.

In another general aspect, a personal hygiene device includes a brush configured to cleanse a rectal area of a user after a toilet use, and a bottle body configured to hold fluid, wherein the personal hygiene device is configured to deliver the fluid to the rectal area to facilitate cleaning of the rectal area.

Strands of the brush may have a thickness of 3 mm or greater.

Strands of the brush may include silicon or synthetic polymer.

Strands of the brush may have a height of 3 mm or greater.

Strands of the brush may form a band around an extension tube that delivers the fluid to the rectal area.

A method of manufacturing a personal hygiene device that includes a bottle body, an extension tube and a brush, may involve integrally forming a brush and an extension tube out of an elastic material.

The integral forming of the brush and the extension tube may involve injection molding the brush and the extension tube simultaneously.

In yet another general aspect, a personal hygiene kit includes a bottle body configured to hold fluid, and a first extension tube configured to connect to the bottle body and having one or more orifice configured to release the fluid, a brush disposed on an outer surface of the extension tube.

The general aspect of the personal hygiene kit may further include a second extension tube configured to connect to the bottle body, the second extension tube having a fluid channel configured to receive the fluid from the bottle body and configured to stretch upon receiving the fluid to increase an outer diameter of the second extension tube.

The second extension tube may be configured for insertion into a female body.

The general aspect of the personal hygiene kit may further include a third extension tube configured to deliver an enema into a colon of a user.

Embodiments in accordance with the present invention provide a personal hygiene device comprising: a bottle body configured to hold a fluid, wherein the bottle body comprises: a bellows shaped chamber; a plurality of flaps; and a plurality of bellows straps attached to the plurality of flaps; an extension tube, connected to the bottle body, having an orifice at a proximal end, wherein the orifice is configured to release the fluid; a brush disposed on the extension tube; and a connector to connect the bottle body with the extension tube.

Embodiments in accordance with the present invention provide a personal hygiene assembly comprising: a bottle body configured to hold fluid, wherein the bottle body comprising: a bellows shaped chamber; a plurality of flaps; and a plurality of bellows straps attached to the plurality of flaps; an extension tube, removably coupled to the bottle body.

Other features and aspects will be apparent from the following detailed description, the drawings, and the claims.

BRIEF DESCRIPTION OF THE DRAWINGS

The foregoing and other aspects of the embodiments disclosed herein are best understood from the following detailed description when read in connection with the accompanying drawings. For the purpose of illustrating the embodiments disclosed herein, there is shown in the drawings embodiments that are presently preferred, it being understood, however, that the embodiments disclosed herein are not limited to the specific instrumentalities disclosed. Included in the drawings are the following figures.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Hereinafter, various examples will be described with reference to schematic diagrams. It is to be understood that when an element, such as a layer, region or substrate, is referred to as being "on," "connected to," or "coupled to" another element, it can be directly "on," "connected to," or "coupled to" the other element or other elements intervening there between may be present. In contrast, when an element is referred to as being "directly on," "directly connected to," or "directly coupled to" another element, other elements or layers intervening there between cannot be present. Like numerals refer to like elements throughout. As used herein, the term "and/or" includes any and all combinations of one or more of the associated listed items.

Although terms such as "first," "second," and "third" may be used herein to describe various members, components, regions, layers and/or sections, these members, components, regions, layers, or sections are not to be limited by these terms. These terms are only used to distinguish one member, component, region, layer or section from another member, component, region, layer or section. Thus, a first member, component, region, layer or section discussed in examples below may also be referred to as a second member, component, region, layer or section without departing from the teachings of the examples.

Spatially relative terms such as "above," "upper," "below," and "lower" may be used herein for ease of description to describe one element's relationship to one or more other elements as shown in the figures. It is to be understood that the spatially relative terms are intended to encompass different orientations of the device in use or operation in addition to the orientation depicted in the figures. For example, if the device in the figures is turned over, elements described as being "above" another element or being an "upper" element will then be "below" the other element or will be a "lower" element. Thus, the term "above" can encompass both the above and below orientations depending on the spatial orientation of the device. The device may also be oriented in other ways (for example, rotated 90 degrees or at other orientations) and the spatially relative descriptors used herein are to be interpreted accordingly.

The terminology used herein is for describing various examples only and is not to be used to limit the present disclosure. As used herein, the singular terms "a," "an," and "the" are intended to include the plural forms as well, unless the context clearly indicates otherwise. Further, as used herein, the terms "include," "comprise," and "have" specify the presence of stated features, operations, members, elements, and/or combinations thereof, but do not preclude the presence or addition of one or more other features, operations, members, elements, and/or combinations thereof.

In the drawings, due to manufacturing techniques and/or tolerances, for example, modifications of the shape shown may result. Thus, the examples described herein are not to be construed as being limited to the specific shapes of regions shown herein, but are to be construed as including changes in shape that occur during manufacturing. The features of the examples described herein may be combined in various ways as will be apparent to one of ordinary skill in the art. Further, although the examples described below have a variety of configurations, other configurations are possible as will be apparent to one of ordinary skill in the art.

Figure 2A:
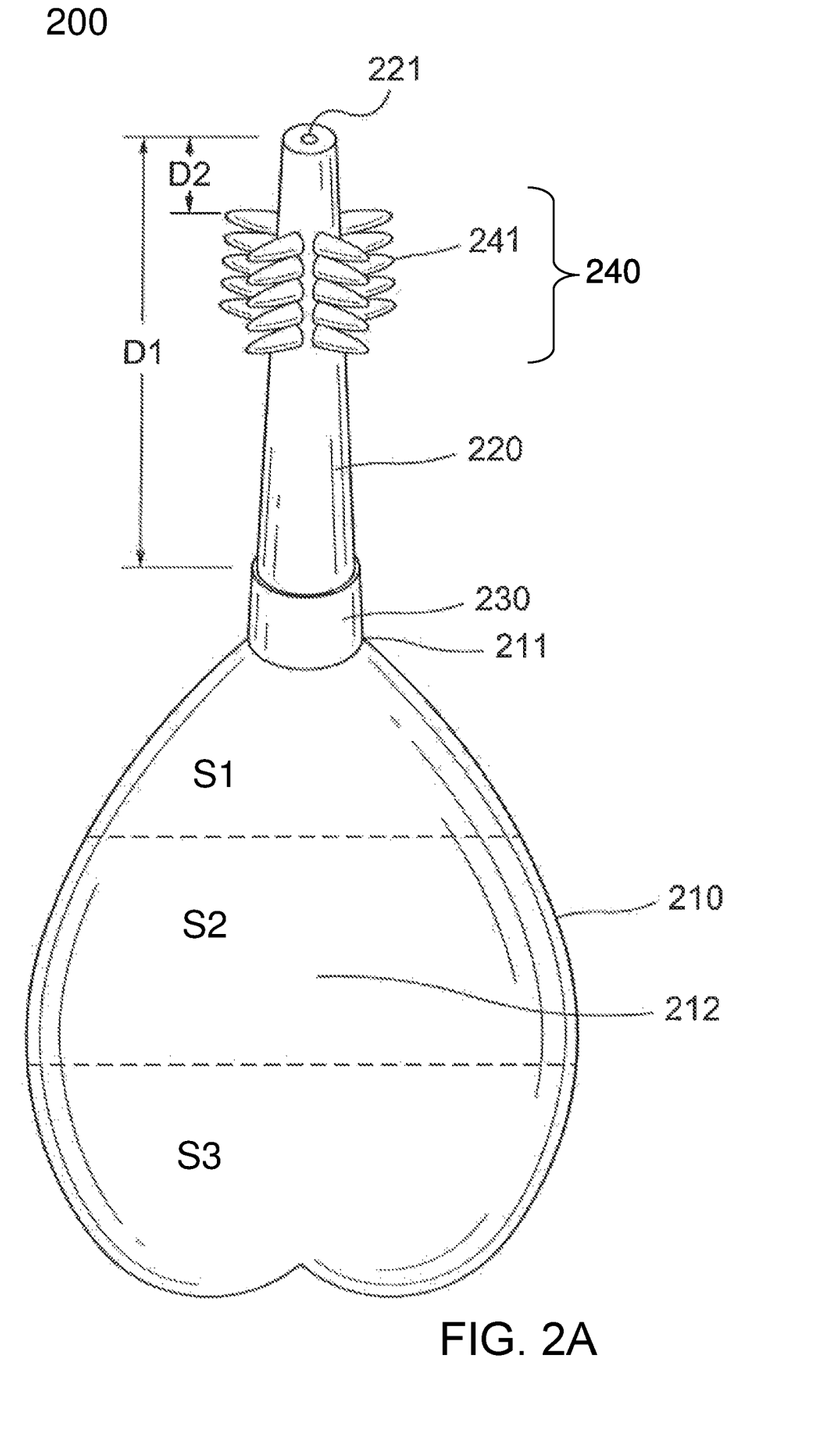
FIG. 2A is a diagram illustrating an example of a personal hygiene device according to the present description.

FIG. 2A illustrates a personal hygiene device 200 according to one example of the present description. The personal hygiene device 200 includes a bottle body 210, an elongated portion in the form of an extension tube 220, and a connector 230 that connects and hermetically seals the bottle body 210 to the extension tube 220. In one example, at least a portion of bottle body 210 may be formed from a material that is sufficiently flexible (and formed in sufficient physical dimensions) to be squeezed by a user in order to force out fluid from within bottle body 210 during normal expected usage. In another example, at least a portion of bottle body 210 may be formed from a material that is sufficiently flexible (and formed in sufficient physical dimensions) to retain its size and shape when not being squeezed by a user. In another example, the connector 230 is made of a hard plastic, separately from the extension tube 220 and the bottle body 210. However, in another example, the connector 230 may be integrally formed with either the extension tube 220 or the connector 230. In yet another example, the bottle body 210, the extension tube 220, and the connector 230 may be formed of the same material or formed integrally.

Referring to FIG. 2A, a brush 240 is positioned on the extension tube 220. According to this example, the brush 240 surrounds the extension tube 220 along its central axis in 360 degrees, and the brush 240 is positioned distal to an orifice 221 located at a tip of the extension tube 220. According to various examples, a length D1 of the extension tube 220 may range between 5 cm to 30 cm, 5 cm to 20 cm, or 5 cm to 10 cm; and the distance D2 between the orifice 221 and the brush 240 may range between 1 cm to 5 cm, or 2 cm to 3 cm. The brush 240 may have bristles or strands 241 that are made of silicon, flexible rubber, elastomer, soft plastic or other synthetic polymer that is flexible and elastic. The flexibility of strands 241 is not necessarily the same as the flexibility of bottle body 210. The strands 241 of the brush 240 may be made of hypoallergenic material free of phthalates and bisphenol-A (BPA). For example, the strands 241 of the brush 240 may be made of ultra-hygienic silicon that is nonporous and resistant to bacteria buildup. The strands 241 of brush 240 may have a thickness of approximately 2 mm to 10 mm, 2 mm to 8 mm, or 3 mm to 5 mm, for example. When the strand 241 has a thickness of less than 1 mm and is made of a hard plastic material, the brush 240 may cause irritations to skin. According to one example, the length of the strands 241 may range between 3 mm to 30 mm, 3 mm to 20 mm, or 3 mm to 10 mm. According to one example, the tip of the strands 241 may have rounded corners. However, the shape of the strands 241 of the brush 240 is not limited thereto.

In the example illustrated in FIG. 2A, the bottle body 210 is made of silicon, rubber or soft synthetic polymer. The shape of the bottle body 210 is designed to allow easy squirting of fluids in the bottle body 210 by squeezing of the bottle body 210 by one hand. The thickness of the bottle body 210 may be adjusted such at it is thicker near the bottle opening 211 and thinner at a hand-pressure surface 212 located at a central portion of the bottle body 210. Further, the girth of the bottle body 210 may decrease toward the bottle opening 211 in order to allow a maximum amount of fluid to be pressed out of the bottle body 210. Dividing the height of the bottle body into three equal-height sections of S1, S2, S3, the top section S1 of the bottle body 210 may include only 20% of less of the fluid volume when the bottle body 210 is full. The middle section S2 may be designed to contain 35% or more of fluid volume. The bottom section S3 may be designed to contain 33% or more of fluid volume. On the contrary, the top section S1 of the bottle body 210 may be formed with 33% or more, or 35% or more, of plastics or materials of the entire bottle body 210 by mass. The middle section S2 may be made of 33% or less, or 30% or less, of plastics or materials of the entire bottle body 210 by mass. In FIG. 2, the bottle body 210 has an external shape of a heart. However, the shape of the bottle body 210 is not limited thereto.

Figure 2B:
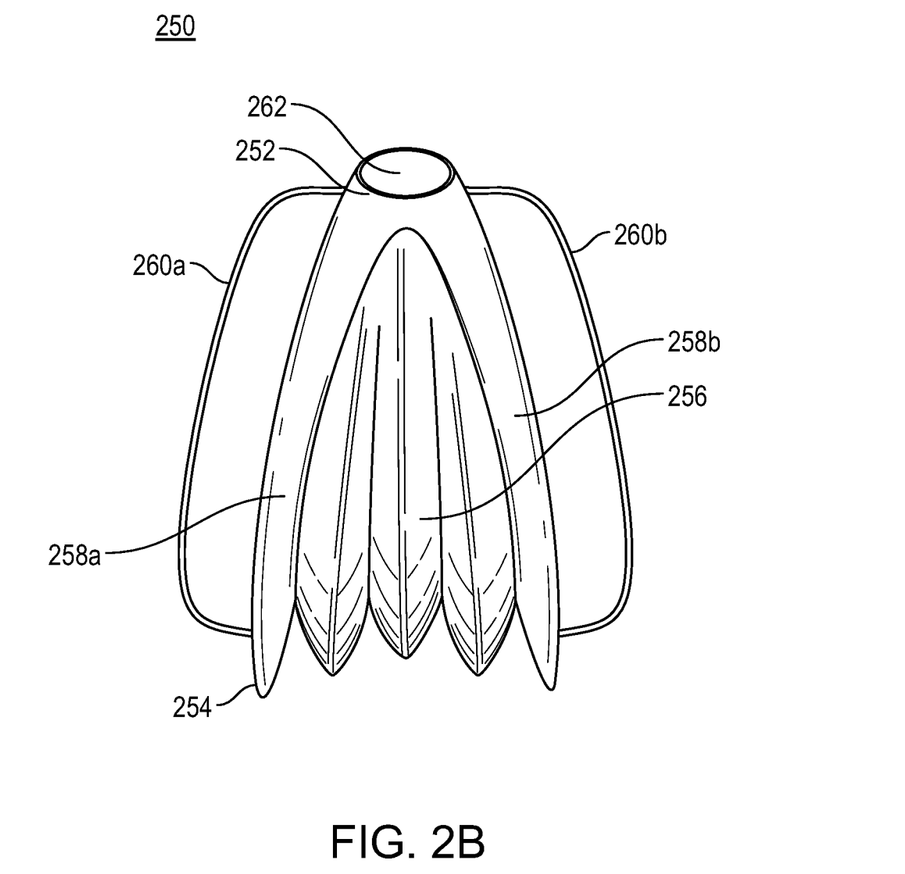
FIG. 2B is a diagram illustrating an example of a bottle body of the personal hygiene device according to the present description.

FIG. 2B illustrates a bottle body 250 of the personal hygiene device 200, according to another embodiment. The bottle body 250 may comprise a proximal end 252 and a distal end 254. Further, the bottle body 250 may comprise a bellows shaped chamber 256 and a plurality of flaps 258a and 258b. The bellows shaped chamber 256 may be joined with the flaps 258a and 258b from two sides enclosing the bellows shaped chamber 256. The bellows shaped chamber 256 may be contracted when a pressure is applied on the flaps 258a and 258b, and on the other hand, the belows shaped chamber 256 may be expanded when the pressure is released from the flaps 258a and 258b. In an embodiment, the bottle body 250 may be formed from a material that is sufficiently flexible (and formed in sufficient physical dimensions) to be squeezed by a user in order to force out a fluid and/or air from within the bottle body 250 during normal expected usage. In another embodiment, the bottle body 250 may be formed by a resilient material, such as, but not limited to, a silicon, a soft rubber plastic, an elastomeric material, a natural rubber, and so forth that may be easily deformable upon an application of a pressure and may regain an original shape after the pressure is removed.

In an embodiment, a shape of the bottle body 250 may be designed to allow easy squirting of the fluid in the bottle body 250 by squeezing of the flaps 258a and 258b of the bottle body 250 by using one hand. In an embodiment of the present invention, an external shape of the bottle body 250 may be, but not limited to, a heart, a bulb, a circle, and so forth. Embodiments of the present invention are intended to include or otherwise cover any shape of the bottle body 250, including known, related art, and/or later developed technologies. According to an embodiment, a color of the bottle body 250 may be, but not limited to, a green, and so forth. Embodiments of the present invention are intended to include or otherwise cover any color of the bottle body 250, including known, related art, and/or later developed technologies.

Further, in an embodiment, the bottle body 250 may be, but not limited to, a bellows device, a douche bulb type device, and so forth. Embodiments of the present invention are intended to include or otherwise cover any type of the bottle body 250, including known, related art, and/or later developed technologies.

Further, the bottle body 250 may comprise a plurality of bellows straps 260a and 260b attached to the flaps 258a and 258b of the bottle body 250. In an embodiment, the bellows strap 260a and 260b may be used to mechanically control the flow of a fluid and/or air from the bottle body 250. In an embodiment, a first end of the bellows strap 260a may be attached onto the flap 258a at the distal end 254 of the bottle body 250, and second end of the bellows strap 260a may be attached onto the flap 258a at the proximal end 252 of the bottle body 250. Similarly, a first end of the strap 260b may be attached onto the flap 258b at the distal end 254 of the bottle body 250, and a second end of the bellows strap 260b may be attached onto the flap 258b at the proximal end 252 of the bottle body 250. In an embodiment, the bottle body 250 may comprise an opening 262 at the proximal end 252 that may be blocked or capped by the tightening of the straps 260a and 260b to restrict the flow of the fluid and/or the air. The opening 262 may be blocked by tightening the bellows straps 260a and 260b when the bellows straps 260a and 260b are pulled in an outward direction from the bottle body 250, opposite to each other.

In another embodiment, the bellows straps 260a and 260b of the bottle body 250 may be used to tie the personal hygiene device 200 with a body part of a user. The body part of the user may be, for example, but not limited to, a waist, a leg, a thigh, and so forth. In an embodiment, the bellows straps 260a and 260b may be used to significantly eliminate a refractory period to eject most of the fluid by tightening the straps 260a and 260b.

According to an embodiment, the bellows straps 260a and 260b may be formed integrally with the flaps 258a and 258b of the bottle body 250. According to another embodiment, the bellows straps 260a and 260b may be removably attached with the flaps 258a and 258b of the bottle body 250.

According to embodiments, the bellows straps 260a and 260b may be made of, but not limited to, a hard plastic, a soft rubber plastic, an elastomeric material, a metal, a rubber, and so forth. Embodiments of the present invention are intended to include or otherwise cover any material of the bellows strap 260, including known, related art, and/or later developed technologies.

Now, the operation of the personal hygiene device will be briefly discussed. The shape and position of the brush 240 on the connector 230 allows a person with back injury to cleanse his rectal area without having to reach the rectal area with his hands and without having to use a toilet paper. After a toilet use, the person may squeeze the bottle to release the fluid in the bottle.

The brush 240 may be formed integrally with the extension tube 220 or formed of silicon or flexible rubber and permanently joined to the extension tube 220. However, the present description is not limited thereto. In another example, the brush 240 may be detachably attached to the extension tube 220 via methods known to those skilled in the art. For instance, a locking mechanism may be provided via a notch at the base of the brush 240 and a protrusion at the extension tube 220.

The extension tube 220, the brush 240, the connector 230 and the bottle body 210 may be made of a synthetic material that allows periodic cleaning. For example, the extension tube 220, the brush 240, the connector 230 and the bottle body 210 may be disassembled and submerged in a chlorinated water or beach solution to maintain hygiene of the personal hygiene device 200.

Figure 3A:
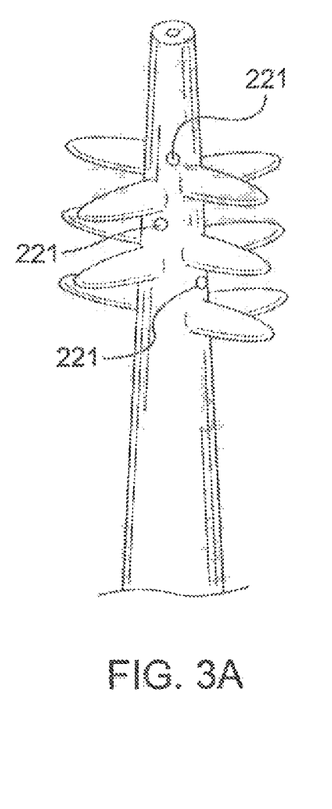
FIG. 3A is a magnified perspective view of the personal hygiene device illustrated in FIG. 2A.

FIG. 3A illustrates another example of an extension tube 220. The extension tube 220 of FIG. 3A may be detachably attached to a bottle body 210 via a connector 230. As illustrated in FIG. 3A, in this example, a plurality of orifices 221 are disposed along a middle portion of the extension tube 220. In this example, no orifice is provided at the tip of the extension tube 220 so as to prevent diversion of fluid from the bottle body 210 and to maintain good water pressure as the water exits from the orifices 221 distributed between the strands 241 of the brush 240.

Figure 3B:
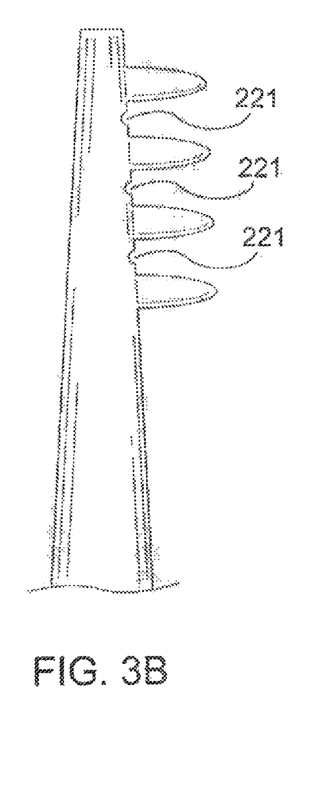
FIG. 3B is a perspective view of another example of an extension tube of a personal hygiene device according to the present description.

FIG. 3B illustrates yet another example of an extension tube 220. In this example, the brush 240 is disposed on one side of the extension tube 220. The orifice is disposed at a tip of the extension tube 220. However, the location of the orifice is not limited thereto. In another example, a plurality of orifices may be distributed between the strands 241 of the brush 240.

Figure 3C:
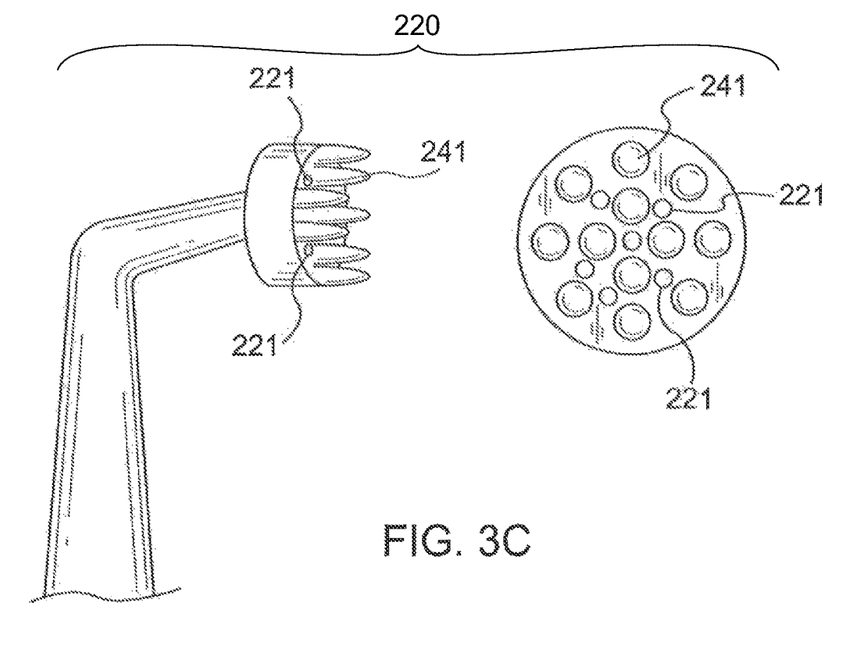
FIG. 3C is a perspective view of an example of an extension tube of a personal hygiene device according to the present description.

FIG. 3C illustrate yet another example of an extension tube 220. In this example, the extension tube 220 is not straight. For example, the extension tube 220 may be bent at predetermined fixed angle. In another example, the extension tube 220 may be adjustably bent within a range of angles by use of a pleated portion of the extension tube 220. The angle of bending, either predetermined or adjustable, may be within a range of 30 degrees to 90 degrees. In another example, the extension tube 220 may be formed with a curve. The extension tube 220, if curved, may be curved around an axis of curvature perpendicular to a lateral (i.e., lengthwise) axis of the extension tube 220. The total length of the extension tube 220 may be 20 to 40 cm, or 20 to 30 cm. The extension tube 220 may be made of a soft plastic or a hard plastic. A plurality of orifices 221 may be positioned at a tip of the extension tube 220. The orifices 221 may be distributed between a plurality of strands 241 of brush 240. The number of strands 241 may range between 3 to 20, or 6 to 18, or about 12, as illustrated in FIG. 3C.

Figure 3D:
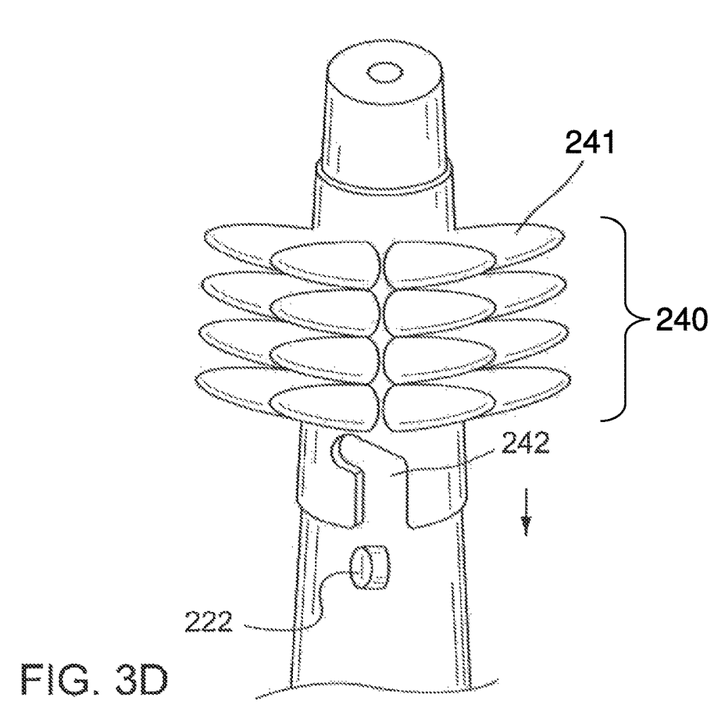
FIG. 3D is a magnified view of an example of an extension tube of a personal hygiene device according to the present description.

FIG. 3D illustrates a magnified view of an example of an extension tube 220 in which a protrusion 222 is formed on the outer surface of the extension tube to mate with a notch 242 of the brush 240. In this example, the brush 240 can be detachably mounted to the extension tube 220. The detachable arrangement of the brush 240 allows brush 240 to be disposed of, separate from the rest of the personal hygiene device 200, when the brush is soiled. The mounting method for attaching the brush 240 on the extension tube 220 is not limited to the illustrated example; in another example, other methods conceivable by those skilled in the art may be employed.

Figure 3E:
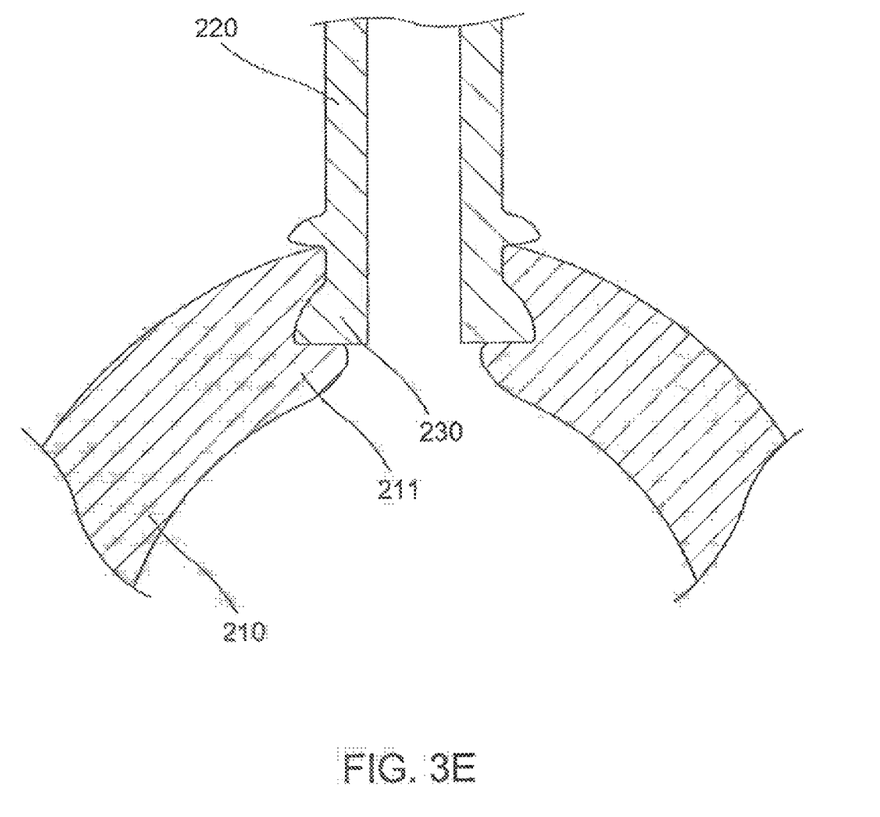
FIG. 3E is a cross-sectional view of an example of a connector of a personal hygiene device according to the present description.

FIG. 3E illustrates a cross-sectional view of an example of a connector 230 of a personal hygiene device. Unlike the connector 230 illustrated in FIG. 2, the connector 230 illustrated in FIG. 3E is integrally formed with the extension tube 220. The connector 230 comprises two ring-shaped protrusions that encircle the connection tube 220, and these protrusions mate with grooves provided in the bottle opening 211. Thus, the connector 230 can seal the fluid inside the bottle body 210 without using many parts, thereby reducing manufacturing costs.

Figure 3F:
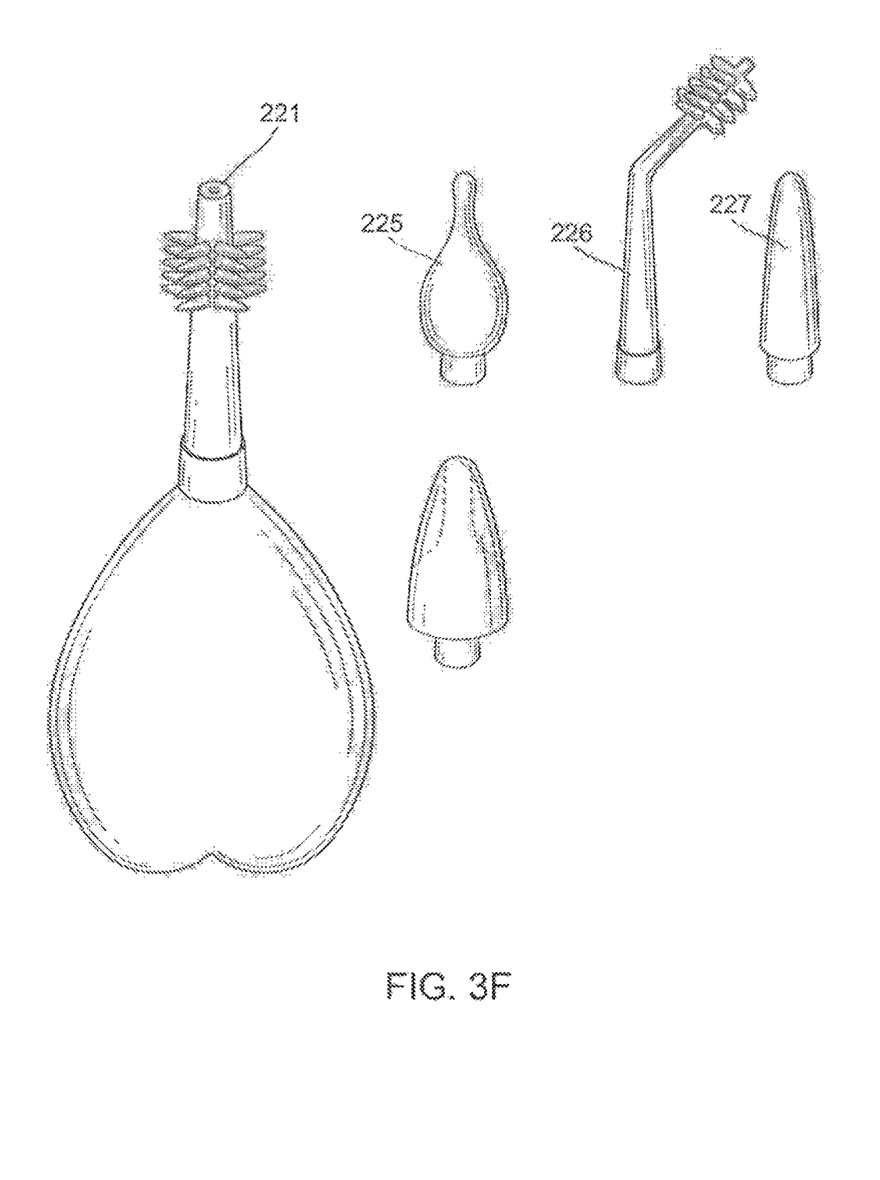
FIG. 3F is a perspective view showing a set of extension tube that may be used with a personal hygiene device according to the present description.

FIG. 3F a perspective view showing a set of extension tube that may be used with a personal hygiene device according to the present description. In this example, the extension tube 220 having a brush 240 may be exchanged with a variety of extension tubes 225, 226 and 227 based on need. For example, the extension tube 225 may be used by a patient with vaginismus to allow an insertion of the extension tube 225 into a female body, and the extension tube 226 may be used by a patient with joint issues to easily squirt fluid without reaching to the back of the body. The extension tube 227 may be used to squirt enema by insertion into rectum in patients with severe gastrointestinal issues. The extension tube 225 for vaginismus may be made of a stretchy material without an orifice 221. When the bottle body 210 is squeezed while the extension tube 225 is installed, the fluid in the bottle body 210 may cause the extension tube 225 to increase in diameter, thereby providing therapeutic benefits to patients. On the other hand, when extension tube 227 is installed on the bottle body 210, the bottle body 210 may be filled with an enema. Squeezing the bottle body 210 can release the enema into the colon of a patient. The extension tube 227 does not include a brush. According to this example, the personal hygiene device 200 may be provided as a kit with a variety of extension tubes 220, 225, 226, 227, so that the user can select the most appropriate extension tube based on a given circumstance. While an example with four types of extension tubes is illustrated, the number and type of extension tubes may be adjusted based on specific needs.

According to an embodiment, the bottle body 250 (shown in FIG. 2B) may be used in combination with an extension tube 225 (shown in FIG. 3F). The straps 266a and 266b may be used to restrict the flow of a fluid and/or air from the bottle body 250 by tightening the straps 266a and 266b, as discussed above. In another embodiment, a removable and attachable cap (not shown) may be used to restrict the flow of the fluid and/or the air from the bottle body 250 by attaching the cap (not shown) to the opening 262 of the bottle body 250. Further, after restricting the flow of the fluid and/or the air, a suitable extension tube such as, but not limited to, the extension tube 220, the extension tube 225, the extension tube 226, the extension tube 227, or any suitable size extension tube may be installed on the bottle body 250. In an exemplary scenario, a patient having vaginismus may use the bottle body 250 in combination with the extension tube 225 (as shown in FIG. 3F). The extension tube 225 may be inserted into the patient's body and when a pressure is applied on the flaps 258a and 258b, the bellows shaped chamber 256 (as shown in FIG. 2B) may be squeezed and the fluid and/or the air within the bottle body 250 may cause the extension tube 225 to increase in diameter, thereby providing therapeutic benefits to the patient. According to an embodiment of the present invention, the extension tube 225 used for the patient having vaginismus may be made of, but not limited to, a stretchy material without an orifice, and so forth.

In another exemplary scenario, a patient having constipation may use the bottle body 250 in combination with the extension tube 220 (as shown in FIG. 3D). The extension tube 220 may be inserted into the patient's body and when a pressure is applied on the flaps 258a and 258b, the bellows shaped chamber 256 may be contracted and the fluid and/or the air within the bottle body 250 may be pushed through the orifice 221 of the extension tube 220 into the patients' body. In an embodiment of the present invention, the extension tube 220 may comprise a detachable arrangement of the brush 240 (as shown in FIG. 3D). The detachable arrangement allows the brush 240 to be disposed of, separate from the extension tube 220 and the extension tube 220 may be used without the brush 240.

According to an embodiment, the bottle body 250, the extension tube 220 and the brush 240 may be configured to cleanse a rectal area and/or a vaginal area of a user. The bottle body 250 may be configured to hold a fluid and/or air that may be delivered through the orifice 221 to the rectal area and/or the vaginal area by applying a pressure on the flaps 258a and 258b (shown in FIG. 2B) to facilitate cleaning of the rectal area, an urinary area and/or the vaginal area.

Figure 4A:
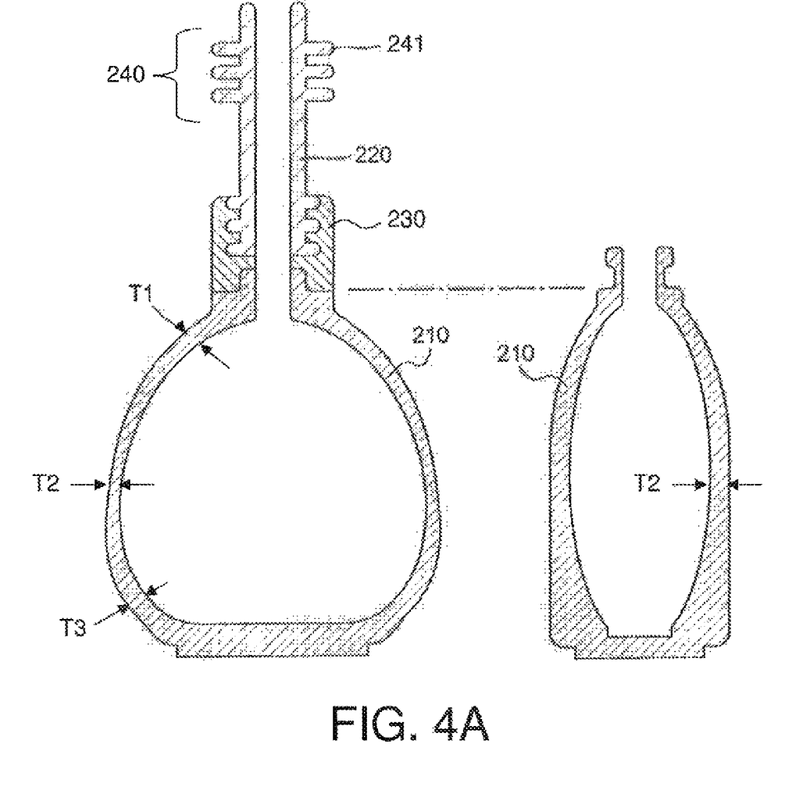
FIG. 4A is a cross-sectional view of an example of a personal hygiene device illustrated in FIG. 2A.

FIG. 4A illustrates a cross-sectional view of a personal hygiene device 200. In this example, the brush 240 is formed integrally with the extension tube 220. The extension tube 220 mates with the bottle body 210 by being screwed thereon via a connector 230. The connector 230 may be made of a hard plastic to maintain the shape of the bottle opening 211. The bottle body 210 may mate with the connector 230 to form water-proof hermetic seal. The thickness T1 of the bottle body 210 at the bottle opening and the thickness T3 of the bottle body 210 at the bottom of the bottle may be greater than the thickness T2 of the bottle body 210 at the central portion of the bottle body 210.

Figure 4B:
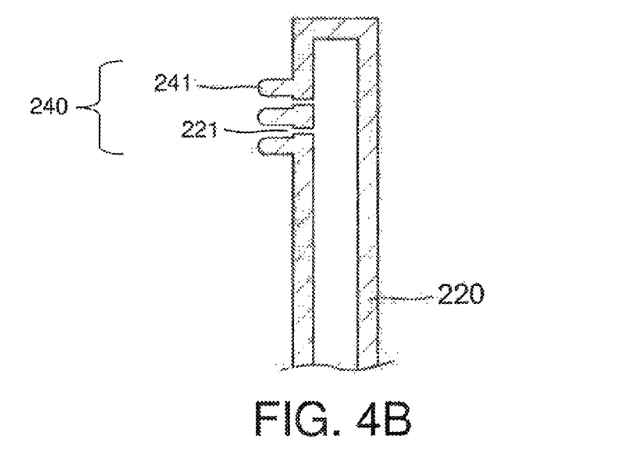
FIG. 4B is a cross-sectional view of an example of a personal hygiene device illustrated in FIG. 3B.

FIG. 4B illustrates a cross-section view of a personal hygiene device 200 illustrated in FIG. 3B. As illustrated, in this example, a plurality of orifices 221 are distributed between the strands 241 of brush 240, while a tip portion of the extension tube 220 is blocked to increase the water pressure of the fluid emerging from the bottle body 210.

Figure 4C:
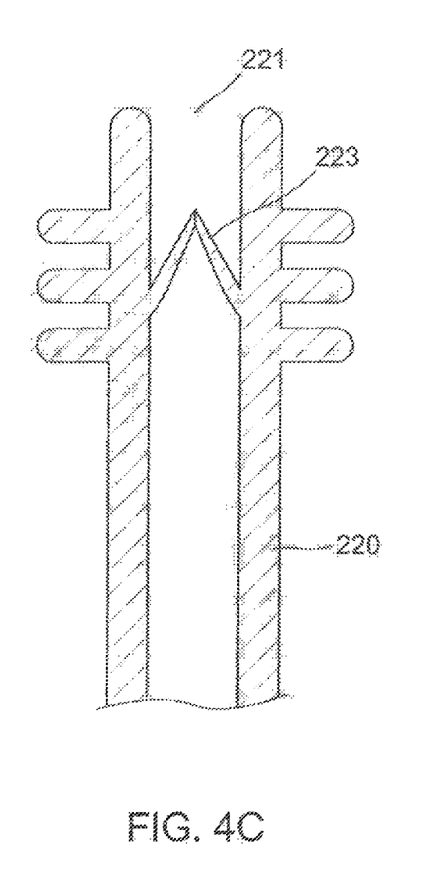
FIG. 4C is a cross-sectional view of another example of a personal hygiene device illustrated in FIG. 2A.

FIG. 4C illustrates a cross-sectional view of yet another example of the personal hygiene device 200 illustrated in FIG. 2. In this example, a valve 223 is disposed within the extension tube 220. The valve 223 is formed of a silicon, rubber, soft plastic, or other synthetic material that allows flaps of the valve 223 to open in response to rising water pressure exerted by fluid pushed out from the bottle body. In this example, the valve 223 is positioned away from the orifice 221 located at the tip of the extension tube 220 so as to prevent the valve 223 from being contaminated by inadvertent contact with the rectum area. For example, the valve 223 may be distanced from the tip of the extension tube 220 by approximately 2 cm or more, 1 cm or more, or 5 mm or more. The valve 223 may prevent the backflow of fluid from outside into the bottle body 210, thereby maintaining inadvertent contamination of fluid inside the bottle body 210.

Figure 4D:
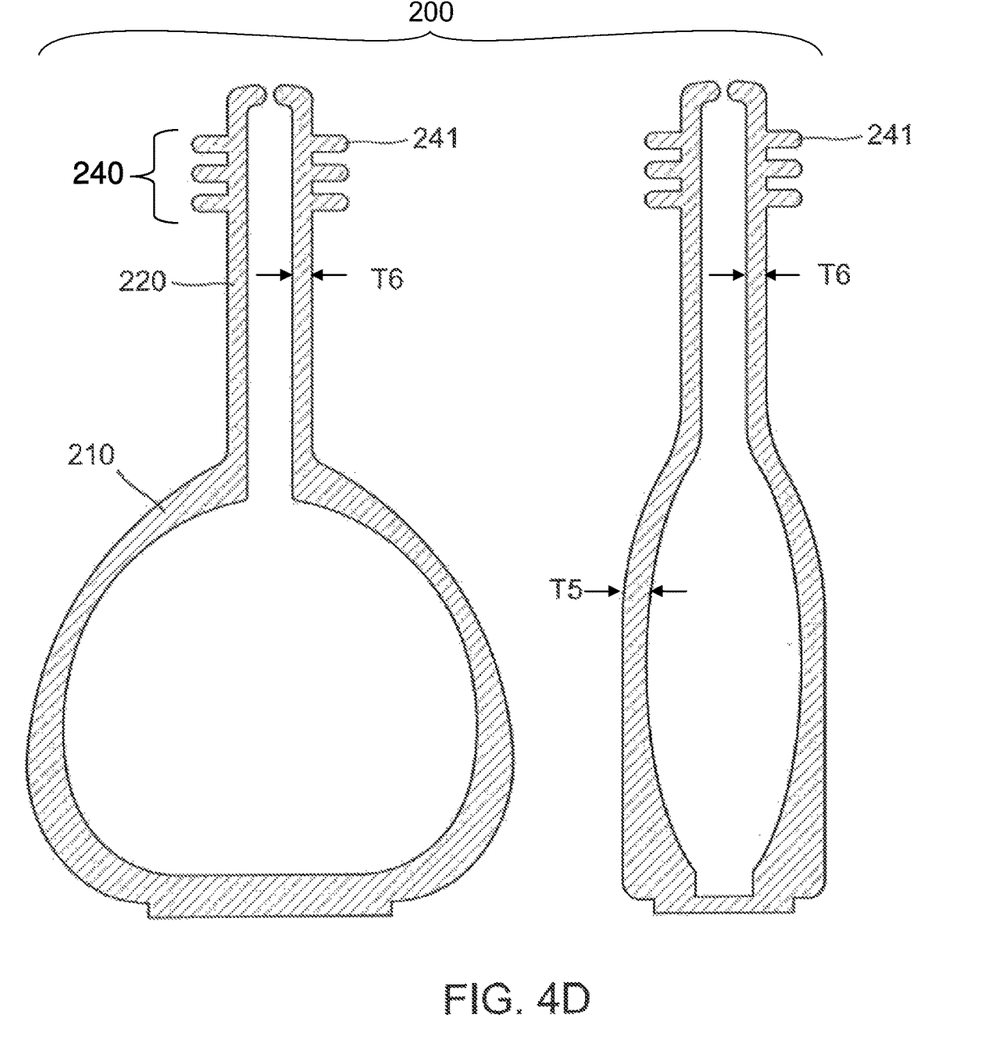
FIG. 4D is a cross-sectional view of another example of a personal hygiene device according to the present description.

FIG. 4D illustrates a cross-sectional view of yet another example of a personal hygiene device 200. In this example, a bottle body 210, an extension tube 220, and a brush 240 are integrally formed, such that each portion is permanently joined to each other. The bottle body 210, the extension tube 220, and the brush 240 may be formed of a same material, such as a soft plastic, silicon, rubber or other synthetic polymer having flexibility and elasticity. The flexibility of portions of the extension tube 220 and the brush 240 may be adjusted by varying the thickness of each portion. In this example, the central portion of the bottle body 210 has a thickness T5 that is less than a thickness T6 of the extension tube 220, and the strands 241 of the brush 240 has a broad but flat configuration, such that the strands 241 are soft. The tips of each strands 241 are rounded to reduce irritation of skin.

The personal hygiene device 200 may be made from injection molding a portion of or an entire personal hygiene device 200. The molding material maybe silicon, soft plastic, rubber, elastomer, plastics including elastomer or other synthetic polymer having flexibility and elasticity. The flexibility of the brush 240 and the bottle body 210 may be adjusted by making the strands 241 and the central portion of the bottle body to have a thickness that is less than that of the extension tube 220 and the brim of the bottle opening 211.

Figure 4E:
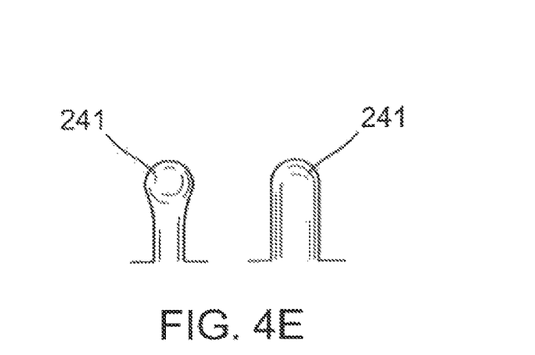
FIG. 4E is a diagram comparing two cross-sectional views of a strand of a brush taken at 90 degrees from each other.

FIG. 4E illustrates two cross-sectional views of a strand 241 of a brush 240 taken at 90 degrees from each other. The strand 241 has a broad but flat configuration, such that the brush strands would be flexible. Further, the tip of the strand 241 is round to prevent irritation of skin.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation.

Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A personal hygiene device comprising:
a bottle body configured to hold fluid, wherein the bottle body comprises:
a bellows shaped chamber having a dispensing opening;
at least two flaps positioned on opposite sides of the bellows shaped chamber; and
at least two bellows straps attached to the at least two flaps such that when the bellows straps are pulled in an outward direction the dispensing opening is restricted;
an extension tube, connected to the dispensing opening, having an orifice at a proximal end, wherein the orifice is configured to release the fluid;
a brush disposed on the extension tube; and
a connector to connect the bottle body with the extension tube.

2. The personal hygiene device of claim 1, wherein the at least two bellows straps are removably attached to the bottle body.

3. The personal hygiene device of claim 1, wherein the brush is disposed on an outer surface of the extension tube.

4. The personal hygiene device of claim 1, wherein the brush is disposed at a proximal end of the extension tube.

5. The personal hygiene device of claim 1, wherein the extension tube is integrally coupled to the bottle body to form a single device.

6. The personal hygiene device of claim 1, wherein the extension tube is removably coupled to the bottle body.

7. The personal hygiene device of claim 1, wherein the connector hermetically seals the bottle body to the extension tube.

8. The personal hygiene device of claim 1, wherein the orifice is disposed at a tip of the extension tube.

9. The personal hygiene device of claim 1, wherein the orifice is disposed along the outer surface of the extension tube.

10. The personal hygiene device of claim 1, wherein the extension tube is curved around an axis of curvature perpendicular to a lateral axis of the extension tube.

11. The personal hygiene device of claim 1, wherein the extension tube is bent at an angle between 30 degrees and 90 degrees.

12. The personal hygiene device of claim 1, further comprising a valve disposed within the extension tube, configured to open in response to rising fluid pressure exerted by fluid pushed out from the bottle body.

13. The personal hygiene device of claim 1, wherein a thickness of the bottle body proximate to the extension tube, and the thickness of the bottle body at a bottom of the bottle body, is greater than the thickness of the bottle body at a central portion of the bottle body.

14. The personal hygiene device of claim 1, wherein the brush is configured to cleanse a rectal area of a user after a toilet use.

15. A personal hygiene assembly comprising:
a bottle body configured to hold fluid, wherein the bottle body comprises:
a bellows shaped chamber having a dispensing opening;
at least two flaps positioned on opposite sides of the bellows shaped chamber; and
at least two bellows straps attached to the at least two flaps such that when the bellows straps are pulled in an outward direction the dispensing opening is restricted;
an extension tube, removably coupled to the dispensing opening; and
a connector to connect the bottle body with the extension tube.

16. The personal hygiene assembly of claim 15, wherein the extension tube comprises a device selected from a group consisting of a first device having an orifice configured to release the fluid and a second device having no orifice.

17. The personal hygiene assembly of claim 16, wherein the second device comprises a stretchy material.

18. The personal hygiene assembly of claim 15, wherein the extension tube is configured to be inserted into a body cavity.

19. The personal hygiene device of claim 15, wherein the at least two bellows straps are removably attached to the bottle body.

* * * * *